United States Patent
Nahabedian et al.

(10) Patent No.: US 6,810,533 B1
(45) Date of Patent: Nov. 2, 2004

(54) VISOR WITH INVERTED DISPLAY MATERIAL

(76) Inventors: David C. Nahabedian, 4 Justin Rd., Natick, MA (US) 01760; Mark Avedikian, 148 Valley Rd., Needham, MA (US) 02492; K. Vasken Babigian, 324 Arlington St., Watertown, MA (US) 02472

( * ) Notice: Subject to any disclaimer, the term of this patent is extended or adjusted under 35 U.S.C. 154(b) by 0 days.

(21) Appl. No.: 10/409,999

(22) Filed: Apr. 9, 2003

(51) Int. Cl.⁷ ............................................. A42C 5/04
(52) U.S. Cl. ................... 2/209.3; 2/DIG. 2; 40/329; D2/876
(58) Field of Search .................... 2/12, DIG. 2, 171, 2/183, 171.1, 181, 209.13, 181.4, 209.3, 195.1, 195.4, DIG. 11, 195.2, 411; 40/329; D2/876

(56) References Cited

U.S. PATENT DOCUMENTS

| | | | |
|---|---|---|---|
| 4,192,017 A | * | 3/1980 | Fay ................................. 2/12 |
| 4,262,367 A | * | 4/1981 | Herrin ............................. 2/12 |
| 4,416,633 A | * | 11/1983 | Gulack ........................ 434/188 |
| D282,118 S | * | 1/1986 | Mengwasser ................. D2/871 |
| 5,131,094 A | * | 7/1992 | Ackerman ....................... 2/12 |
| 5,177,811 A | * | 1/1993 | Ulrich ......................... 2/209.7 |
| 5,181,277 A | | 1/1993 | Sherman |
| 5,239,704 A | | 8/1993 | Cornelio |
| 5,253,364 A | | 10/1993 | Robinson |
| 5,418,981 A | | 5/1995 | Miner |
| D364,953 S | * | 12/1995 | Bell ............................. D2/882 |
| 5,509,144 A | | 4/1996 | Soergel |
| 5,613,246 A | | 3/1997 | Alexander |
| 5,845,339 A | * | 12/1998 | Ashley et al. ............... 2/195.6 |
| 5,893,170 A | | 4/1999 | Garza |
| 5,901,370 A | * | 5/1999 | Linday ............................ 2/10 |
| 5,903,923 A | * | 5/1999 | Morse et al. ................. 2/195.1 |
| 6,272,689 B1 | * | 8/2001 | Kronenberger ............. 2/175.1 |
| 6,408,443 B1 | | 6/2002 | Park |
| 6,449,773 B1 | * | 9/2002 | Shwartz et al. .............. 2/195.1 |
| 6,588,021 B2 | * | 7/2003 | Kronenberger ............. 2/195.1 |
| 2002/0000001 A1 | * | 1/2002 | Hall McKenzie ............ 2/195.2 |
| 2002/0108162 A1 | * | 8/2002 | Bolds-Leftridge ............ 2/49.1 |
| 2003/0106127 A1 | * | 6/2003 | Shwartz et al. ................. 2/12 |

* cited by examiner

Primary Examiner—Rodney M. Lindsey
(74) Attorney, Agent, or Firm—O'Connell Law Firm

(57) ABSTRACT

A visor construction with inverted display material for enabling the visor to be worn of a head of a wearer in an upside down orientation while providing an upright disposition of display material. The visor has a header panel with a first, outwardly facing surface and a second surface for being disposed adjacent to the head of the wearer. An arcuate bill is fixed to the header projecting transversely from the first, outwardly facing surface of the header panel. A strap, resiliently deflectable legs, or any other appropriate arrangements can be employed to retain the header panel and the arcuate bill relative to the wearer's head. Display material is oriented oppositely to the visor construction thereby enabling the visor construction to be worn upside down while retaining the display material in an upright orientation.

12 Claims, 5 Drawing Sheets

VISOR WITH INVERTED DISPLAY MATERIAL

FIELD OF THE INVENTION

The present invention relates generally to headwear. Stated more particularly, this patent discloses and protects a visor with inverted display material that can be worn in an upside-down orientation while nonetheless providing an upright depiction of the display material.

BACKGROUND OF THE INVENTION

The prior art has, of course, disclosed numerous visor structures and designs. A typical visor provides a bill and a means for retaining the bill relative to a wearer's head. The means for retaining the bill relative to the wearer's head in some cases comprises a pair of resiliently deflectable opposed legs for frictionally engaging opposite sides of the wearer's head. In other cases, the means for retaining the bill relative to the wearer's head takes the form of a strap for entirely encircling the head of the wearer. An adjustment means, such as a buckle arrangement or hook and loop members, can enable the size of the loop defined by the strap to be adjusted to accommodate wearer's with different head sizes.

In traditional practice, such visors will be worn with the bill situated with its proximal portion adjacent to the wearer's forehead and the body of the bill projecting therefrom. As such, the bill, which is often laterally bowed, can protect the wearer's face against the potentially harmful effects of the sun while providing comfortable and useful shade to the wearer's eyes. In many respects, it is additionally advantageous that visors provide these and further benefits without overlying the top of the wearer's head. As such, the visor avoids matting down the wearer's hair while, among other things, allowing heat to escape from the top of the wearer's head, which can be particularly advantageous when the visor is worn during hot weather and during physical activity.

Most visors further include a header that is transverse to the bill for being disposed against the wearer's forehead. Where the visor is retained by a strap, the header can be a contiguous segment of the strap and can be formed from a textile, a polymer, or substantially any other type of material. Where the visor has opposed legs, the header can comprise a separate piece of cloth, plastic, or other material. Alternatively, the header can be formed integrally with the bill, such as by being molded therewith as a single polymeric member.

In any case, by virtue of its orientation relative to the bill, the body of the header provides a display area or portion that can have logos, graphics, text, or any other display material applied thereto. However, many visors additionally or alternatively have logos, graphics, text, and other display material applied elsewhere on the visor, such as along the strap, on one or both opposed legs, and even on the bill itself. By way of example, many visors have the logos and/or the names of sports teams displayed on their headers, straps, legs, or other outwardly facing surface or surfaces while other visors retain corporate names or logos. These and substantially any other display materials can be applied to the visor header, the strap, one or both opposed legs, and/or on the visor bill whether by being printed thereon, by being stitched therein, by being secured in the form of a patch, or by any other suitable method. Display material normally has an upright orientation and an upside-down orientation. Where the display material has an orientation, it is of course disposed on the visor such that it will displayed in an upright orientation when the visor is worn in what can be considered a traditional or upright manner with the header against the wearer's forehead and the bill projecting from under the header.

However, it has become fashionable among certain groups of wearers to wear visors in a markedly different manner, namely, upside down and, at times, backward. When a traditional visor is worn upside down, the display material disposed thereon will necessarily be displayed upside down. With that, the display material, whether it be a team logo, an advertisement, or any other displayed element, loses its effectiveness as an advertisement or other display since the observer sees only an overturned image.

As a result, it has become clear to the present inventors that a visor construction that can enable a wearer to wear the visor in an upside down orientation while nonetheless providing an upright depiction of display material would be advantageous to wearers, advertisers, sports teams, and any other person or entity that would be well served by the provision of such an orientation of display material.

SUMMARY OF THE INVENTION

Advantageously, the present invention is founded on the most broadly stated object of providing a visor construction that enables the visor to be worn in an upside down orientation while providing an upright depiction of display material.

A related object of the invention is to provide a visor construction that demonstrates added utility to advertisers, sports teams, and wearers by not frustrating the intent of the advertisers, sports teams, and wearers to have the depicted logo, advertisement, or other material depicted in an upright and legible manner.

An additional object of the invention is to provide a visor construction that is unique as compared to the prior art thereby to present a stylish improvement over prior art visor arrangements.

These and further objects and advantages of the invention will become obvious not only to one who reviews the present specification and drawings but also to one who has an opportunity to make use of an embodiment of the present invention for a visor with inverted display material. However, it will be appreciated that, although the accomplishment of each of the foregoing objects in a single embodiment of the invention may be possible and indeed preferred, not all embodiments will seek or need to accomplish each and every potential object and advantage. Nonetheless, all such embodiments should be considered within the scope of the present invention.

In carrying forth these and further objects, a most basic embodiment of the visor construction is founded on a header panel with a body portion that has a first, outwardly facing surface and a second surface for being disposed adjacent to the head of the wearer. A bill is fixed to the header panel projecting transversely from its first, outwardly facing surface, and a means is provided for retaining the header panel and the bill relative to the wearer's head. The bill is normally arcuate such that it has a first face presenting a convex surface and an opposite second face presenting a concave surface.

The visor construction can be considered to have an upright orientation wherein the arcuate bill is disposed with the convex surface facing generally upwardly and the concave surface facing generally downwardly such that the bill presents an arc with a middle portion disposed above downturned end portions. In such a case, the majority of the header is normally disposed above the bill. The visor also has an upside down orientation wherein the bill is disposed with the concave surface facing generally upwardly and the convex surface facing generally downwardly such that the bill presents an arc with a middle portion disposed below upturned end portions.

Display material, such as a logo, textual material, or any other possible material that one might seek to display on a visor, is disposed on the visor, such as on the display portion of the header panel, on a strap or legs that act as means to retain the visor in place on a wearer's head, on the arcuate bill, or on any other outwardly facing surface of the visor. Under the present invention, the display material has an upright orientation and an upside down orientation and is oriented upside down as compared to the visor construction. Under this arrangement, the visor construction can be worn on a wearer's head in an upside down orientation while nonetheless providing an upright depiction of the display material.

As noted above, the header panel and the bill can be retained relative to the wearer's head by any suitable means, such as a strap that defines a loop for encircling the wearer's head. Where such a strap is provided, the visor construction can further include a means for adjusting the size of the loop defined by the strap. That means could comprise a buckle arrangement, a hook and loop combination, a button combination, or any other suitable arrangement. In certain embodiments, the header panel can simply comprise a segment of the strap, such as by having the two elements formed from one or more pieces of textile material.

In an alternative construction, the means for retaining the header panel and the bill relative to the wearer's head can comprise first and second resiliently deflectable legs for frictionally engaging opposite sides of the wearer's head. Under such an arrangement, the header panel, the bill, and the first and second resiliently deflectable legs could be formed unitarily of a polymeric material.

The particular content of the display material is of little consequence. For example, it can comprise a logo, name, or slogan of a sports team, company, school, or any other person or entity, an artistic element, or any other possible type of display. The display material could be disposed on the header portion, on the strap or legs, on the bill, or on any other outwardly facing surface in any appropriate manner, including by printing, by stitching, or by securing a patch.

One will appreciate that the foregoing discussion broadly outlines the more important features of the invention to enable a better understanding of the detailed description that follows and to instill a better appreciation of the inventors' contribution to the art. Before an embodiment of the invention is explained in detail, it must be made clear that the following details of construction, descriptions of geometry, and illustrations of inventive concepts are mere examples of the many possible manifestations of the invention.

DETAILED DESCRIPTION OF PREFERRED EMBODIMENTS

As with many inventions, the present invention for a visor arrangement with inverted display material can assume a wide variety of embodiments. However, to assist those reviewing the present disclosure in understanding and, in appropriate circumstances, practicing the present invention, certain exemplary embodiments of the visor arrangement are described below and shown in the accompanying drawing figures.

Figure 1:
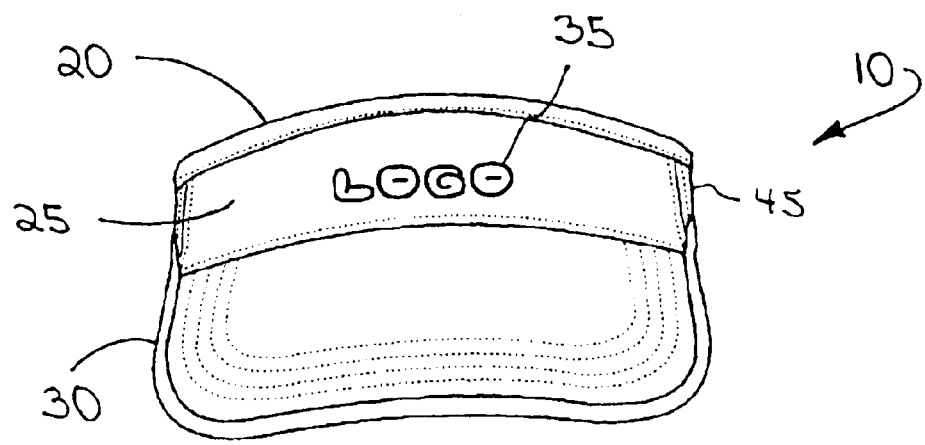
FIG. 1 is a view in front elevation of a visor construction according to the prior art in an upright orientation.

Looking more particularly to the drawings, a prior art visor construction 10 is shown in FIG. 1. There, one sees that the visor 10 is founded on an arcuate bill 30 that is fixed to a header 20. In this embodiment, the arcuate bill 30 and the header 20 can be retained relative to a wearer's head by a strap 45. The header 20 in this exemplary visor 10 comprises a band of material with a first, outwardly facing surface that provides a display portion 25 and a second surface for being disposed against the head of a wearer. A logo, an advertisement, text, or any other display material 35 can be applied substantially anywhere on the visor 10, including on the display portion 25 of the header 20. The display material 35 could comprise a team name or logo; a corporate name, slogan, or logo; an artistic design; a textual display; or any other possible type of display. In this case, the visor 10 simply employs the term LOGO to provide an example of display material 35.

Figure 2:
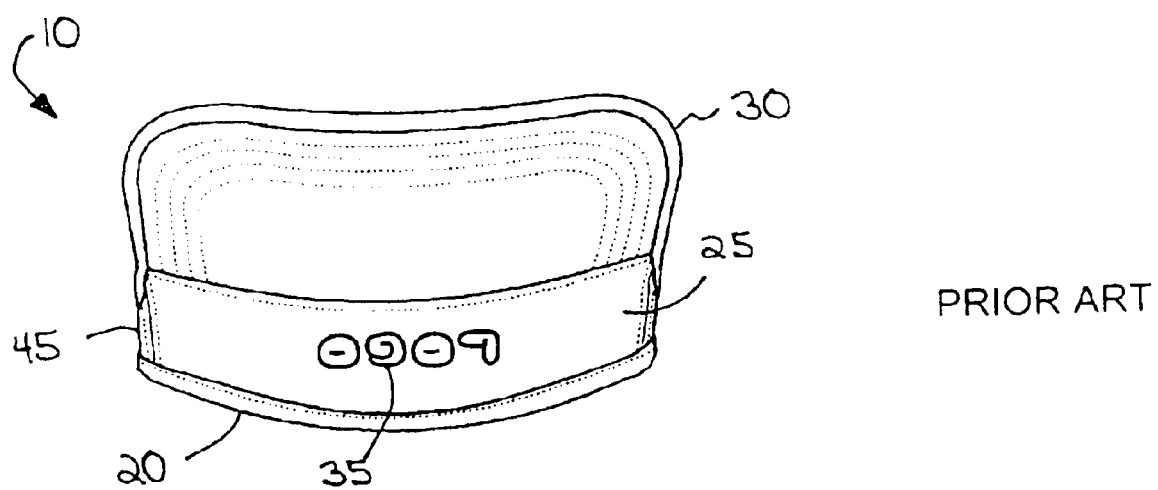
FIG. 2 is a view in front elevation of the visor construction of FIG. 1 in an upside down orientation.

It will be appreciated that, as with substantially any material that might be displayed, the display material 35 in FIG. 1 has an upright orientation, which is how the display material 35 was designed to be viewed, and an upside down orientation, which is contrary to the way the display material 35 was designed to be viewed. Similarly, the visor 10 has an upright or traditional orientation as is shown in FIG. 1, which is how the visor 10 was originally designed to be worn, wherein the arcuate bill 30 is disposed with its convex surface facing generally upwardly and its concave surface facing generally downwardly such that the bill 30 presents an arc with a middle portion disposed above downturned end portions. In such a case, the majority of the header 20 is normally disposed above the bill 30. The visor 10 also has an upside down orientation as is shown in FIG. 2 wherein the bill 30 is disposed with the concave surface facing generally upwardly and the convex surface facing generally downwardly such that the bill 30 presents an arc with a middle portion disposed below upturned end portions.

Under the prior art, the orientations of the display material 35 and the visor 10 in general are aligned such that, when the visor 10 is worn in an upright orientation as in FIG. 1, the display material 35 also will be disposed in its upright, intended orientation. However, as FIG. 2 shows, when the visor 10 is worn in a non-traditional, but presently stylish, upside-down orientation, the display material 35 will be displayed in an unintended, upside down orientation thereby frustrating the shared intentions of the wearer and the originator of the display material 35, such as the advertiser, the sports team, the artist, and any other potential design originator.

Advantageously, the present invention overcomes this major disadvantage thereby to further the shared intentions of the wearer and the design originator. A visor 40 according the present invention is shown in FIGS. 3 through 6 to include again an arcuate bill 30 that projects from a header 20. A means for retaining the arcuate bill 30 and the header 20 relative to a wearer's head is provided in the form of a strap 45. The strap 45 in this case incorporates a fastening and adjustment means 65 that can comprise a buckle arrangement, a hook and loop combination, a button combination, or any other appropriate configuration for enabling the size of the loop defined by the strap 45 to be adjusted. The header 20 again provides a display portion 25 on which display material 35 with a given orientation can be applied by printing, by stitching, by being secured in the form of a patch, or by any other desired method.

Figure 3:
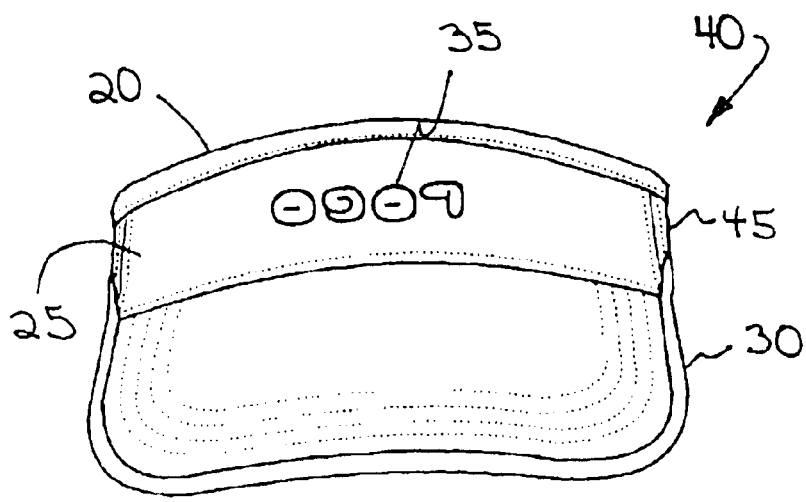
FIG. 3 is a view in front elevation of a visor construction according to the present invention in an upright orientation.
Figure 4:
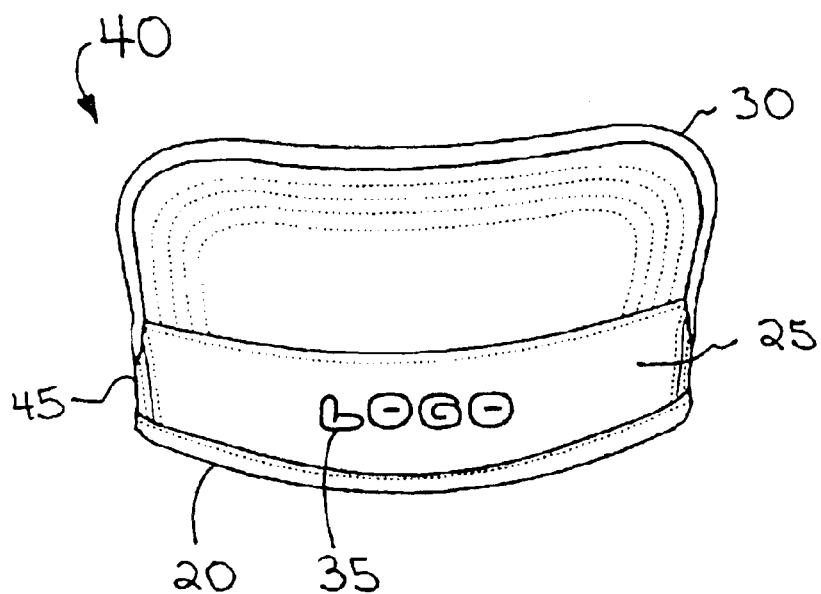
FIG. 4 is a view in front elevation of the visor construction of FIG. 3 in an upside down orientation.
Figure 5:
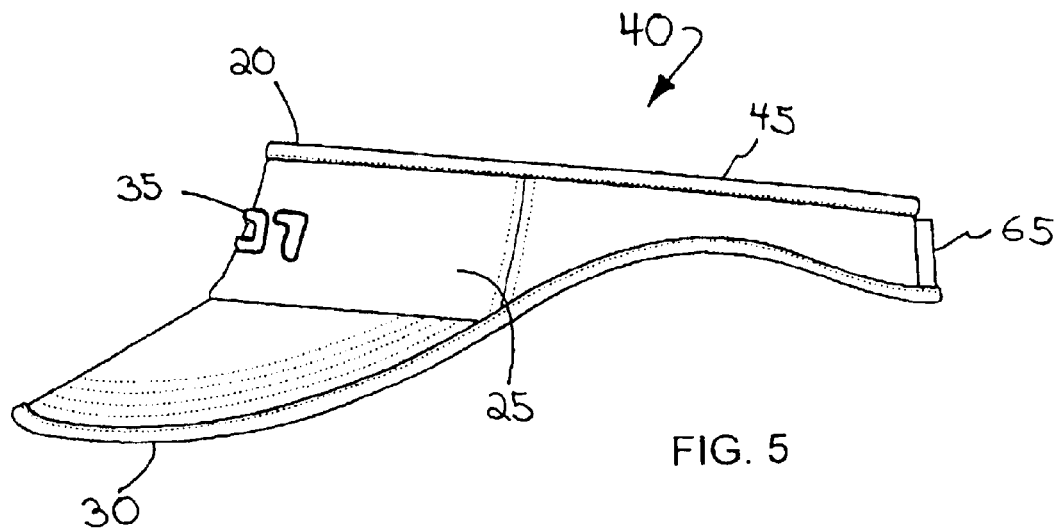
FIG. 5 is a view in side elevation of the visor construction of FIG. 3 in an upright orientation.
Figure 6:
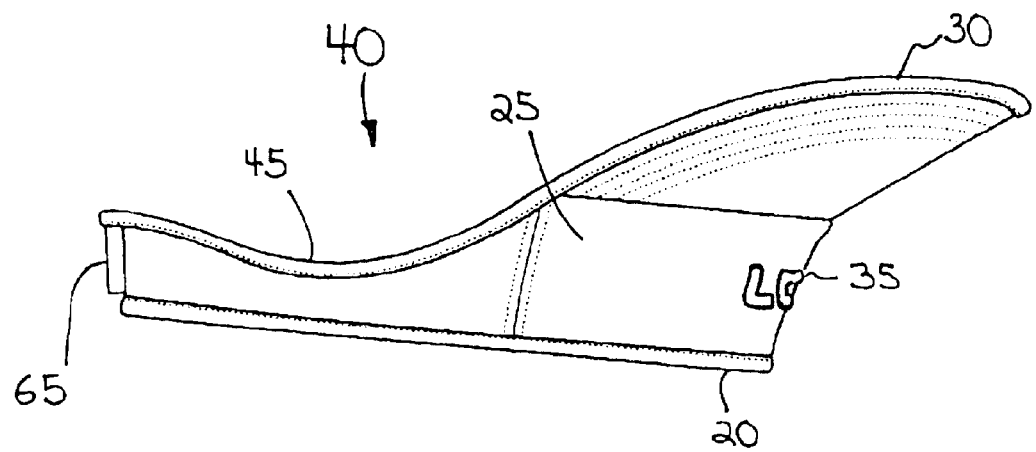
FIG. 6 is a view in side elevation of the visor construction of FIG. 3 in an upside down orientation.

In this case, however, the display material 35 has an orientation that is opposite to the orientation of the visor 40 in general such that the display material 35 is disposed in an upside down orientation when the visor 40 is disposed in an upright orientation as is shown in FIGS. 3 and 5. However, when the visor 40 is worn in the non-traditional, upside down orientation of FIGS. 4 and 6, whether with the arcuate bill 30 disposed to the front of the wearer's head or to the rear, the display material 35 will be disposed, in an upright orientation. As a result, the team logo, the corporate slogan, or whatever else forms the display material 35 will be properly displayed and fully discernable.

Figure 7:
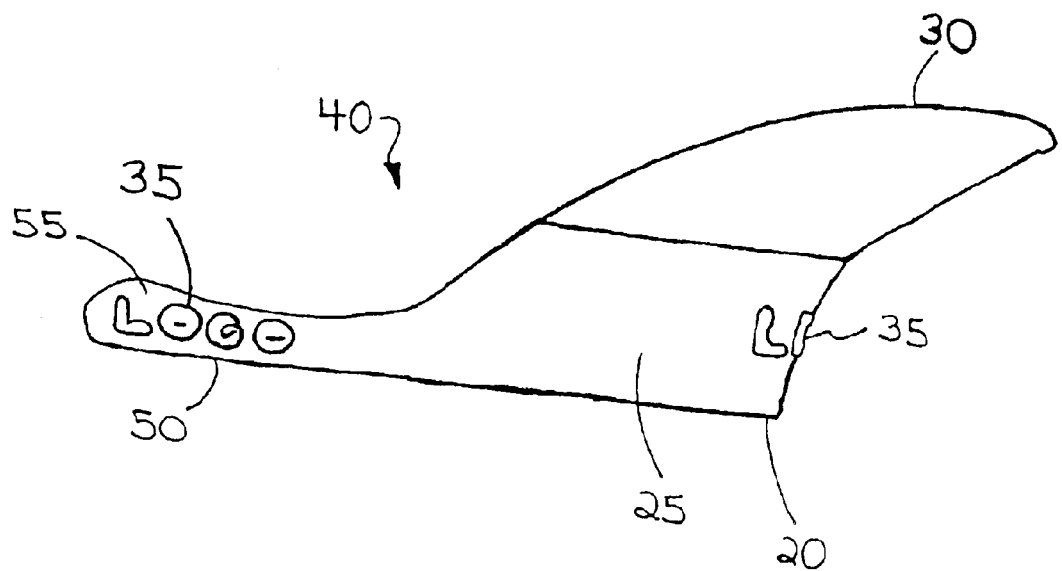
FIG. 7 is a view in side elevation of an alternative visor construction according to the present invention in an upside down orientation.

Of course, the invention can pursue different embodiments. For example, as is shown in FIG. 7, the strap 45 can be replaced as the means for retaining the arcuate bill 30 and the header 20 relative to the wearer's head with a pair of opposed, resiliently deflectable legs 50. In use, the legs 50 can be disposed to opposite sides of the wearer's head to retain the visor 40 by frictional engagement between the legs 50 and the wearer's head. The display material 35 again has an orientation that is opposite to the orientation of the visor 40 in general such that the display material 35 will be disposed in an upright orientation when the visor 40 is worn in an upside down orientation.

Figure 8:
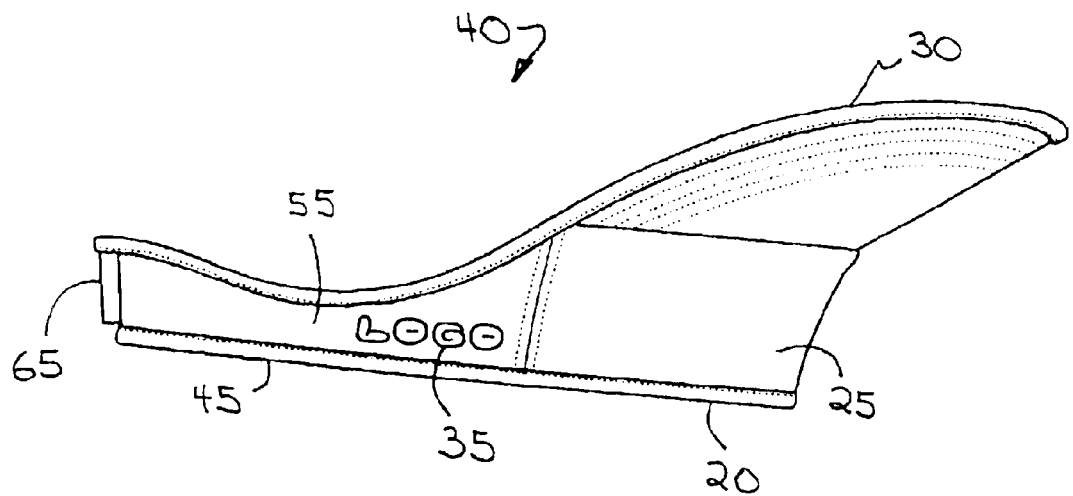
FIG. 8 is a view in side elevation of another visor construction under the present invention.
Figure 9:
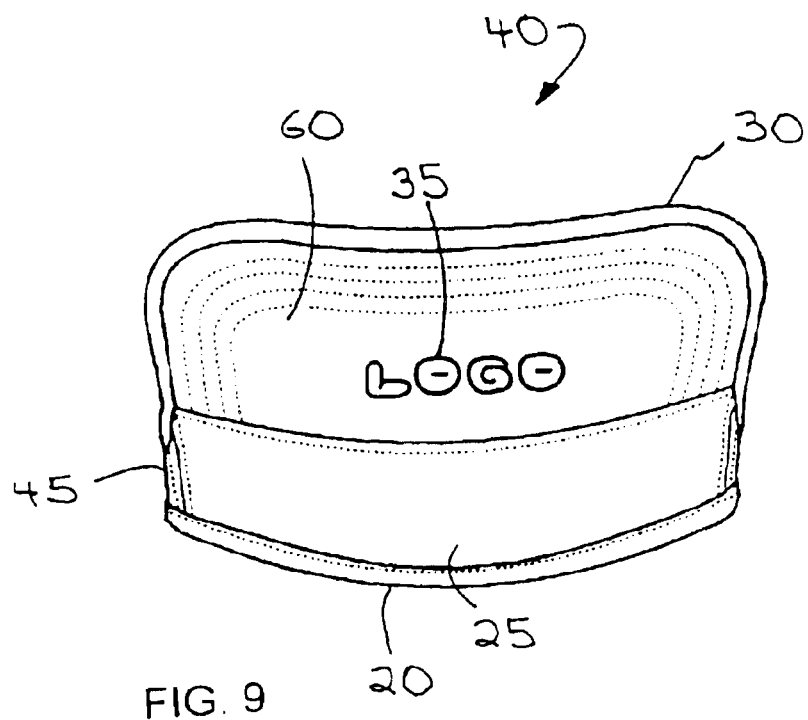
FIG. 9 is a view in front elevation of yet another visor construction according to the present invention.
Figure 10:
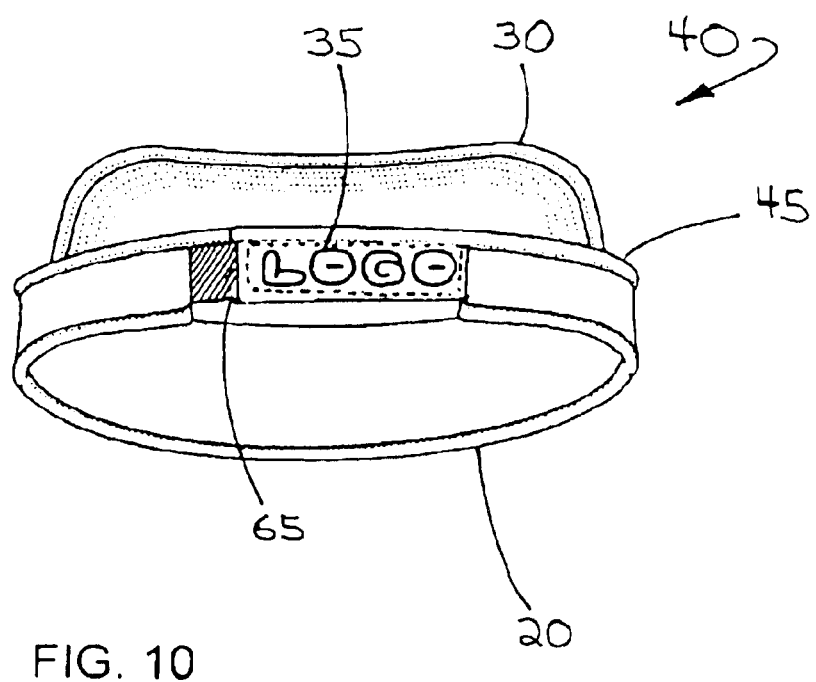
FIG. 10 is a view in rear elevation of still another embodiment of the present invention for a visor construction.

Of course, the location of the display material 35 on the visor 40 can vary within the scope of the invention. Indeed, it can be disposed on substantially any outwardly visible surface or portion of the visor 40. For example, as FIG. 7 shows, display material 35 can be disposed on an outwardly visible portion or display area 55 of one or both of the resiliently deflectable legs 50 that retain the visor 40 relative to a wearer's head. Alternatively, where a strap 45 is provided for retaining the visor 40 relative to a wearer's head, display material 35 can be disposed on any outwardly visible display area or portion 55 of the strap 45. For example, the display material 35 can be disposed along a side portion of the strap 45 as is shown in FIG. 8 or over the rearmost portion of the strap 45, such as overlying the fastening and adjustment means 65 as is shown in FIG. 10 where the fastening and adjustment means comprises a hook and loop arrangement. Even further, as FIG. 9 shows, display material 35 can additionally or alternatively be disposed on an outwardly visible portion or display area 60 of the arcuate bill 30.

Of course, elements of display material 35 can be applied on and even across multiple locations on any given visor 40. Elements of display material 35 can be entirely independent of one another. Alternatively, elements of display material 35 on various portions of the visor can be interdependent and can even comprise continuous or discontinuous segments of an overall design. In each case, the display material 35 can be applied to the visor 40 in any appropriate manner.

It will be appreciated that the particular structure of the visor 40 and the materials employed to form that structure 40 are of little consequence to the present invention. As such, the visor 40 can have a header 20 formed from any flexible, rigid, or semi-rigid material or combination of materials. The same is true of the arcuate bill 30 and the strap 45 or the legs 50. Under one construction, for example, the strap 45 and the header 20 can be formed from a single type of material, such as a flexible textile or substantially any other suitable material. The arcuate bill 30 can be formed with a rigid substrate that could be enveloped in one or more layers of textile material. Under another construction, the arcuate bill 30, the header, and the legs 50 or the strap 45 can be formed unitarily, such as by molding or any other suitable method, from a polymer, such as plastic. These and many further materials and combinations of materials are possible.

With a plurality of exemplary embodiments of the present invention for a visor 40 with inverted display material 35 disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims are intended to define the scope of protection to be afforded to the inventors. However, those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also equivalents thereof.

We claim as deserving the protection of Letters Patent:

1. A visor construction with inverted display material for enabling the visor construction to be worn on a head of a wearer in an upside down orientation while providing an upright disposition of display material, the visor construction comprising:

a header panel with a first, outwardly facing surface and a second surface for being disposed adjacent to a head of a wearer;

an arcuate bill fixed to the header panel wherein the bill projects transversely from the second surface of the header panel and wherein the arcuate bill has a convex surface and an opposite concave surface;

a means for retaining the header panel and the bill relative to a head of a wearer;

wherein the visor construction has an upright orientation wherein the arcuate bill is disposed with the convex surface of the arcuate bill facing generally upwardly and the concave surface of the arcuate bill facing generally downwardly such that the arcuate bill presents an arc with a middle portion disposed above downturned end portions and wherein the visor construction has an upside down orientation wherein the arcuate bill is disposed with the concave surface of the arcuate bill facing generally upwardly and the convex surface of the arcuate bill facing generally downwardly such that the bill presents an arc with a middle portion disposed below upturned end portions; and display material disposed on an outwardly visible surface of the visor construction wherein the display material has an upright orientation comprising an orientation in which the display material is designed to be viewed and an upside down orientation comprising an orientation contrary to the orientation in which the display material was designed to be viewed wherein the orientation of the display material is opposite to the orientation of the visor construction whereby the display material will be disposed in an upright orientation when the visor construction is disposed in an upside down orientation.

2. The visor construction of claim 1 wherein the means for retaining the header panel and the arcuate bill relative to a head of a wearer comprises a strap that defines a loop for encircling a wearer's head.

3. The visor construction of claim 2 further comprising a means for adjusting a size of the loop defined by the strap.

4. The visor construction of claim 3 wherein the means for adjusting the size of the loop defined by the strap is chosen from the group consisting of a buckle arrangement, a hook and loop combination, and a button combination.

5. The visor construction of claim 2 wherein the header panel comprises a segment of the strap.

6. The visor construction of claim 5 wherein the header panel and the strap are formed from textile material.

7. The visor construction of claim 2 wherein the display material is disposed at least partially on the strap.

8. The visor construction of claim 1 wherein the means for retaining the header panel and the arcuate bill relative to a wearer's head comprises first and second resiliently deflectable legs for frictionally engaging opposite sides of a wearer's head.

9. The visor construction of claim 8 wherein the header panel, the arcuate bill, and the first and second resiliently deflectable legs are unitarily formed of a polymeric material.

10. The visor construction of claim 8 wherein the display material is disposed at least partially on at least one of the resiliently deflectable legs.

11. The visor construction of claim 1 wherein the display material is disposed at least partially on the header portion.

12. The visor construction of claim 1 wherein the display material is disposed on an outwardly visible surface of the visor construction by a method chosen from the group consisting of printing, stitching, and securing a patch.

* * * * *